United States Patent [19]

Sedun et al.

[11] Patent Number: 5,246,716
[45] Date of Patent: Sep. 21, 1993

[54] FATTY ACID-BASED ANTIFUNGAL COMPOSITION HAVING RESIDUAL ACTIVITY

[75] Inventors: Frederick S. Sedun, Saanichton, Canada; Hellmut E. Kulenkampff, Hameln, Fed. Rep. of Germany

[73] Assignee: W. Neudorff GmbH KG, Emmerthal, Fed. Rep. of Germany

[21] Appl. No.: 818,613

[22] Filed: Jan. 10, 1992

[51] Int. Cl.$^5$ .................. A01N 59/02; A01N 55/02; A01N 37/02

[52] U.S. Cl. .................. 424/713; 424/703; 424/705; 514/78; 514/494; 514/499; 514/502; 514/558; 514/557; 514/560

[58] Field of Search .............. 514/557, 558, 560, 78, 514/494, 499, 502; 424/703, 705, 713

[56] References Cited

U.S. PATENT DOCUMENTS

| | | | |
|---|---|---|---|
| 2,466,663 | 4/1949 | Russ et al. | 514/558 |
| 3,931,413 | 1/1976 | Frick et al. | 514/558 |
| 4,001,400 | 1/1977 | Hager | 514/558 |
| 4,177,288 | 12/1979 | Gohlke | 424/713 |
| 4,179,522 | 12/1979 | Huitson | 514/558 |
| 4,381,194 | 4/1983 | DelliColli et al. | 71/79 |
| 4,496,547 | 1/1985 | Kawashima et al. | 514/25 |
| 4,585,795 | 4/1986 | Linderborg | 514/558 |

FOREIGN PATENT DOCUMENTS 59-2224 1/1984 Japan.
2137090 3/1984 United Kingdom.

OTHER PUBLICATIONS

Zubay, Geoffrey, Biochemistry. Mass., Addison-Wesley Publishing Company, 1983. p. 472.
Chemical Abstracts 102:98193n (1985).
Chemical Abstracts 85(3): 15347x, Jul. 19, 1976.
W. T. Thomson, Agricultural Chemicals, Book IV, p. 21 (1987–1988, Thomson Publications).

Primary Examiner—Allen J. Robinson
Assistant Examiner—John D. Pak
Attorney, Agent, or Firm—Lahive & Cockfield

[57] ABSTRACT

An environmentally compatible, non-phytotoxic antifungal composition is provided having an active ingredient which comprises a fatty acid metal salt having from 4 to 18 carbon atoms. The metal salt may be formed from metals including calcium, copper, magnesium, and zinc. Additional formulation enhancing agents, such as dispersants, wetting agents and gums, are typically included within the composition. The composition is advantageous in that it exhibits a residual fungicidal effect lasting up to 2 months.

11 Claims, No Drawings

FATTY ACID-BASED ANTIFUNGAL COMPOSITION HAVING RESIDUAL ACTIVITY

BACKGROUND OF THE INVENTION

The invention relates to environmentally compatible compositions which protect plants from fungal infection without exhibiting phytotoxic side effects.

Agricultural and horticultural plants are susceptible to infection by pathogenic fungi. Such fungi can severely damage or even kill the infected plants. Many commercially available anti-fungal compositions, like pesticides generally, are petrochemical-based products which are not naturally occurring compounds. As a result, these products do not readily breakdown in the environment, or they do not do so rapidly. While these petrochemical-based fungicides may be effective in preventing fungal infection of many plants, they also pose certain environmental risks, as well as potential health hazards.

Some naturally occurring compounds, such as the sodium and potassium salts of certain fatty acids, have been used as insecticides, herbicides and cryptocides (moss killers). However, the inherent phytotoxicity of these compounds does not render them useful in fungicidal compositions to be applied to living plants. Moreover, because these compounds can be rapidly decomposed by microorganisms, they must frequently be reapplied.

Accordingly, there is a need for an effective, environmentally safe fungicidal composition which is non-phytotoxic and which has residual activity.

It is thus an object of the invention to provide an effective, environmentally compatible fungicidal composition. A further object is to provide such a fungicidal composition which exhibits little or no phytotoxicity. Another object is to provide a fungicidal composition which has residual fungicidal effect on plants to which it is applied. Yet another object is to provide an effective and environmentally safe method of protecting plants from fungicidal infection. Other objects will be apparent to those of ordinary skill in the art upon reading the disclosure which follows.

SUMMARY OF THE INVENTION

The present invention comprises an effective fungicidal composition which is environmentally compatible in that it does not persist in the environment, and which poses few, if any, health hazards to humans, fish and wildlife. Moreover, the composition of the invention exhibits little or no phytotoxicity towards plants to which it is applied, and it provides a residual fungicidal effect on plant surfaces for as long as two months.

The fungicidal composition comprises an active ingredient of one or a mixture of metal salts of alpha monocarboxylic fatty acids having from 4 to 18 carbon atoms. Preferably, the fatty acid active ingredient contains from 6 to 12 carbon atoms. The metals from which the fatty acid metal salt active ingredient may be formed include calcium, copper, iron, magnesium and zinc. Typically, a carrier is included with the active ingredient, and the composition may take the form of a liquid, a gel, or a solid.

The fatty acid metal salt active ingredient may be used as the sole active ingredient or in combination with other active ingredients. Suitable co-active ingredients may include those which broaden the spectrum of fungi against which the composition is effective. Examples of these include sulfur and lecithin-based compositions.

Various formulation enhancing agents may be included in the composition as well. Preferably the fungicidal composition includes a gum, such as a xanthan gum, an acacia gum, a locust bean gum, and/or gels such as gelatin or sodium alginate. Other desirable formulation enhancing agents include dispersants, wetting agents, and a formulation preservative such as a compound having a low freezing point (e.g., propylene glycol, ethylene glycol or glycerine) to prevent the composition from freezing either before or after application.

DETAILED DESCRIPTION OF THE INVENTION

The fungicidal composition of this invention is one which can be applied to plant surfaces and remain fungicidally effective for as long as two months. At the same time, the composition exhibits little or no phytotoxicity with respect to the plants to which it is applied. Moreover, the active ingredient is a naturally occurring compound which is readily broken down in the environment to yield non-toxic constituents.

The composition comprises an active ingredient as well as a carrier and one or more formulation enhancing agents. The active ingredient is preferably one or a mixture of fatty acid metal salts. In another embodiment an additional active ingredient can be used in combination with the fatty acid metal salt active ingredient. The composition may take the form of a liquid concentrate or a wettable powder. Generally, both the liquid concentrate and powder-like compositions are diluted with or dispersed in a carrier such as water before application. Various formulation enhancing additives, such as wetting agents, dispersants, gums, antifreezing agents, and the like may also be included in the composition.

The fatty acid metal salt active ingredient may comprise a metal salt of one or a mixture of alpha monocarboxylic fatty acids having from 4 to 18 carbon atoms. More preferably, the fatty acid metal salts have from 6 to 12 carbon atoms, and most preferably from 8 to 10 carbon atoms. The metal ions from which the salts can be formed include $Mg^{+2}$, $Ca^{+2}$, $Fe^{+2}$, $Fe^{+3}$, $Cu^{+1}$, $Cu^{+2}$ and $Zn^{+2}$. The calcium salts are among the most preferred, especially the calcium salt of octanoic acid ($Ca(C8)_2$), and the calcium salt of nonanoic acid ($Ca(C9)_2$).

To be fungicidally effective, the fatty acid metal salt active ingredient should be used in a concentration range of about 0.05 to 5.0 percent by weight of the total composition. More preferably, the effective range is from about 0.1 to 1.0% by weight. It is noted, however, that the effective amount of the active ingredient will vary depending upon the identity of the fatty acid salt active ingredient used, as some fatty acids are more fungicidally potent than others.

The calcium salts of the fatty acids are presently the most preferred. The minimum concentration believed to be necessary to achieve a fungicidal effect of fatty acid salts is slightly less than 0.1% for calcium octanoate and calcium nonanoate, about 0.2% for calcium heptanoate, 0.5% for calcium hexanoate and calcium decanoate, and about 1% for calcium propionate, calcium butyrate and calcium valerate.

In some embodiments it is also possible to use additional active ingredients in combination with the fatty acid metal salt active ingredient. Sulfur is an example of a useful co-active ingredient which broadens the spectrum of fungi against which the composition is effective. Sulfur is particularly effective in compositions which are intended to control powdery mildew. Sulfur can be used in concentrations from about 50 to 100% of the concentration of the fatty acid metal salt active ingredient. Preferably, sulfur is used at concentration of about 0.1 to 1.0% by weight.

Other co-active ingredients which may be used include lecithin and lecithin-based compositions. These serve to broaden the fungal kill spectrum, and to further reduce the phytotoxicity of the composition. Lecithin and lecithin-based co-active ingredients may be used at concentrations ranging from 5% to 100% of the concentration of the fatty acid metal salt active ingredient. Preferably, lecithin is present at about 25% to 100% by weight of the fatty acid metal salt active ingredient.

Water is a preferred carrier for liquid compositions as well as for granular or powdery compositions which are to be dissolved or dispersed in a liquid before application to plants. Other useful carriers include agricultural petroleum distillates and vegetable oils. Generally, sufficient carrier is used to dilute the concentration of the active ingredient to the desired range.

Exemplary agricultural petroleum distillates include light mineral oils and napthalates. One specific example is Sunspray 6E plus available from Sun Refining and Marketing Company, Philadelphia, Pa. Exemplary vegetable oils include, but are not limited to, cottonseed oil, soybean oil, and canola oil.

Gums and gum-like materials may also be included within the composition as a formulation enhancing agent which serves to assist the active ingredient in remaining on the surface of the plant. Preferred gums include virtually any gum material which is compatible with the active ingredient, and which is also environmentally compatible. The exemplary gums include xanthan gum, acacia gum, and locust bean gum. Suitable commercially available gums include Rhodopol 23 (a xanthan gum) and VanGel B (a magnesium aluminum silicate), both of which are available from R.T. Vanderbilt of Norwalk, Ct. As noted above, gelatin and sodium alginate may be used as well. Gums and gum-like materials may be used in an amount such that the total gum component is present at about 0.02 to 0.3 percent by weight in a composition applied to plants. The concentration of gums in a concentrated formulation may be in the range of about 0.5 to 10% by weight.

Dispersants and wetting agents are also useful in liquid compositions as well as solid compositions which are to be dissolved in or dispersed in liquids before application. Preferred dispersants include Morwet D425 (sodium sulfonate of napthalene formaldehyde condensate), Morwet B (sodium di-isopropyl napthalene sulfonate), and Morwet DB (sodium di-n-butyl napthalene sulfonate), all available from Witco of New York, N.Y.; and sodium napthalene sulfuric acid formaldehydes, such as Darvan No. 1 (available from R.T. Vanderbilt of Norwalk, Ct.). Preferred wetting agents include dioctyl sodium sulfosuccinate-containing compounds, such as Aerosol OT75 and Aerosol OTB, available from American Cyanamid; and nonylphenol ethoxylates such as Macol NP-6, available from Mazer Chem. of Gurnee, Ill. Dispersants may be used in an amount such that they are present at about 0.08 to 0.3 percent by weight in a composition applied to plants, while wetting agents may be present at about 0.02 to 1.5 percent by weight of a composition applied to plants. In concentrated formulations, the dispersants can be present at about 2-15% by weight, and the wetting agents at about 0.5-5% by weight.

Isopropyl alcohol may also be used as a dispersant or wetting agent in liquid formulations. The isopropyl alcohol typically is used in relatively high concentrations (e.g., about 45 to 55% by weight).

Additives which have a low freezing point are also useful in preventing freezing of certain fungicidal compositions, especially liquid based fungicidal compositions. Exemplary anti-freezing agents which can be used with the composition include propylene glycol, ethylene glycol and glycerine. Presently, propylene glycol is a preferred anti-freezing agent. Such agents typically are used at concentration ranges of about 0.1 to 0.3 percent by weight of compositions applied to plants. Concentrated formulations typically include about 2-10% by weight of an anti-freezing agent.

Many variations in the fungicidal composition of the invention are possible, although the presence of an effective amount of a metal salt of an alpha monocarboxylic acid is essential. Where a liquid composition is used the fatty acid active ingredient preferably is dispersed in an aqueous carrier such as water. The liquid form may also include gums, dispersant, wetting agent, and an additive which prevents freezing.

In one embodiment, a dry formulation can be prepared for subsequent dilution in water before application. The dilution in water results in the in situ formation of the fatty acid metal salt. An exemplary formulation includes the following components

| | |
|---|---|
| potassium octanoate | 64.1 g |
| calcium nitrate | 28.9 g |
| Aerosol OTB (Wetting Agent) | 6.0 g |
| Aerosil 200 (flow agent) | 1.0 g |

Upon dilution of the above formulation with water at a ratio of from 1:50 to 1:100, a calcium octanoate active ingredient is formed by reaction between the potassium octanoate and the calcium nitrate. Potassium nitrate is a by-product of the reaction and can be useful as a plant fertilizer. It is noted that sodium octanoate can be substituted for potassium octanoate, and calcium chloride or another calcium salt can be used instead of calcium nitrate. Generally, two moles of potassium octanoate are used for every mole of calcium nitrate.

In the above formulation, Aerosol OTB, commercially available from American Cyanamid, is a dry powder which comprises 85% dioctyl sodium sulfosuccinate and 15% sodium benzoate. Aerosil 200 is commercially available from Degussa Corp. of Teterboro, N.J. and is a silicate-based free flowing agent.

Exemplary liquid formulations include the following concentrated formulations which may be diluted with water (or another carrier instead of water) prior to use to yield a total active ingredient concentration in the range of about 0.1 to 1.0% by weight.

| Component | Amount | |
|---|---|---|
| Formulation A | | |
| Calcium octanoate | 25.0% | (w/w) |
| Morwet D425 (Dispersant) | 4.0 | |
| Aerosol OT75 (Wetting Agent) | 0.9 | |
| Rhodopol 23 (Gum) | 0.2 | |
| Vangel B (Gum) | 0.8 | |
| Propylene glycol | 5.0 | |

| Component | Amount |
|---|---|
| Water | 64.1 |
| Formulation B | |
| Calcium octanoate (C8) | 5.0% |
| Calcium nonanoate (C9) | 5.0% |
| Magnesium octanoate | 5.0% |
| Magnesium nonanoate | 5.0% |
| Morwet D425 | 4.0 |
| Aerosol OT75 | 0.9 |
| Rhodopol 23 | 0.2 |
| Vangel B | 0.8 |
| Propylene glycol | 5.0 |
| Water | 64.1 |
| Formulation C | |
| Calcium octanoate | 10.0% |
| Powered sulfur (Co-active ingredient) | 10.0% |
| Morwet D425 | 4.0% |
| Aerosol OT75 | 0.9% |
| Rhodopol 23 | 0.2 |
| Vangel B | 0.8 |
| Propylene glycol | 5.0 |
| Water | 64.1 |
| Formulation D | |
| Calcium octanoate | 1.0% |
| Isopropyl alcohol | 49.5% |
| Water | 49.5% |

Exemplary dry formulations, dispersible before use in an amount of water sufficient to yield an active ingredient concentration in the range of 0.1 to 1.0 percent weight, are also illustrated below.

| Component | Amount |
|---|---|
| Formulation E | |
| Calcium octanoate | 88.0% |
| Sodium alginate (thickener) | 4.0% |
| Morwet D425 | 4.0% |
| Aerosol OTB | 2.0% |
| Aerosil 200 | 2.0% |
| Formulation F | |
| Calcium octanoate | 80.0% |
| BioBlatt | 15.0% |
| Aerosol OT75 | 4.9% |
| Aerosil 200 | 0.1% |

The BioBlatt composition used in formulation F is commercially available from W. Neudorff CmbH KG of Emmerthal, Germany. This composition is a lecithin-based composition. Although BioBlatt is a liquid, it becomes absorbed by the remaining constituents of Formulation F.

The lecithin component of Formulation F is believed to be effective in reducing the phytotoxicity of the composition and in increasing the fungicidal spectrum of the composition. This composition is effective in controlling powdery mildew, such as the fungus *Erysiphe cichoracearum*.

An important advantage of the composition of the invention is that the fungicidal properties of the composition are residual, lasting for as long as two months. This residual effect is believed to result, in part, from the relatively low solubility in water of the fatty acid metal salts. The solubility of these salts in water is approximately 0.1 to 0.5 g/100 ml of water. In an aqueous formulation various formulation enhancers, such as wetting agents and dispersants keep the active ingredient wetted, dispersed and suspended in the carrier. When applied to a plant the carrier and formulation enhancers are either washed off the plant and/or evaporate. The salt of the fatty acid remains adhered to the plant's surface, sometimes with the aid of gums. By adhering to the plant's surface, the salt of the active ingredient is able to maintain its fungicidal effect for extended periods of time.

The low solubility in water of the fatty acid metal salts also contributes to the low phytotoxicity of the formulation. Low phytotoxicity is essential for the composition as it is applied to plants in order to kill pathogenic fungi, or to prevent their infestation of the plant. Compositions which are phytotoxic as well as fungicidal are not desirable.

The fatty acid metal salt is dispersed in water to form a metal cation and a fatty acid anion. The anion is the agent which is potentially toxic to both fungi and plants. The metal salts of the present invention are much less soluble than are sodium and potassium salts, for example, which are known to be effective herbicidal agents. The nature of the dynamic equilibrium of the fatty acid metal salt in water is such that the anion and the cation concentrations remain constant, provided that there is an excess of the fatty acid metal salt present. An excess of the fatty acid metal salt generally requires a concentration greater than 0.5 g/ml water. The equilibrium concentration of the anion (i.e., about 0.1 to 0.5 g/100 ml of water) is such that it is toxic to fungi but not toxic to the plant.

As noted above, the active ingredient remains adhered to the surface of the plant over a period of time. The active ingredient remains a non-dissociated fatty acid metal salt when it is adhered to the plant in dry form. When rain or other moisture is deposited on the plant the active ingredient dissociates until the concentration of the anion reaches equilibrium. Upon drying, the anion and the cation combine again to form the fatty acid metal salt.

The fungicidal composition of the present invention is a broad range fungicide which is effective against a variety of pathogenic fungi. Examples of common fungi which the composition is effective against include *Botrytis cinerea*, *Rhizoctonia solani* AG 4, *Fusarium oxysporum*, *Pythium* sp., *Aspergillus niger*, *Penicillium digitatum*, *Penicillium* sp, *Venturia inaequilliss*, *Colletotrichum lindemuthianum*, and *Erysiphe communis*.

The following non-limiting examples serve further to describe the invention.

Unless otherwise noted, the following examples were conducted using Exemplary formulation A, diluted as stated in the examples.

EXAMPLE 1

Five branches on each of five Early Gravenstein apple trees were randomly assigned treatments of one of the compositions identified in Table 1. The branches were sprayed to run-off weekly from April 4 until July 3. Thereafter, the branches were sprayed once every ten days until August 12. The apples were harvested at maturity and the effect of Apple Scab caused by *Venturia inaequalis* was evaluated. The data is shown in Table 1.

TABLE 1

| Treatment | Total Apples | Diseased Apples |
|---|---|---|
| 1.0% AI* | 147 | 5% |
| 0.2% AI* | 68 | 60% |
| 0.25% Benomyl | 121 | 35% |

TABLE 1-continued

| Treatment | Total Apples | Diseased Apples |
|---|---|---|
| Untreated (water) | 84 | 86% |

*Denotes concentration of the calcium octanoate active ingredient in the applied Formulation A

EXAMPLE 2

Five branches on each of eight Golden Delicious apple trees were randomly assigned one of the treatments of Table2. The branches were sprayed to run-off weekly from April 4 to July 3. Thereafter, the branches were sprayed once every ten days until August 12. The apples were harvested at maturity and the effect of Apple Scab caused by *Vanturia inaequalis* was evaluated. The data is illustrated in Table 2.

TABLE 2

| Treatment | Total Apples | Diseased Apples |
|---|---|---|
| 1.0% AI | 137 | 13% |
| 0.2% AI | 204 | 84% |
| 0.25% Benomyl | 138 | 94% |
| Untreated (Water) | 110 | 95% |

EXAMPLE 3

Six rows of eight plants of strawberry variety Totem were assigned the following treatments: 1% calcium octanoate $(Ca(C8)_2)$ active ingredient (prepared according to Formulation A), 0.2% Rovral (Iprodione), and untreated (water). The plants were sprayed twice weekly from the onset of flowering to harvest. The berries were stored under 100% relative humidity at room temperature and examined daily for the presence of mold. The effect of grey mold (*Botrytis cinerea*) was evaluated five days after harvest and the data is illustrated in Table 3.

TABLE 3

| Treatment | Proportion of Berries Moldy |
|---|---|
| 1.0% $Ca(C8)_2$ | 9% |
| 0.%2 Rovral | 4% |
| Untreated | 41% |

EXAMPLE 4

One hundred twenty-five blackberry racemes were randomly assigned treatments of 1% calcium octanoate (prepared as in Formulation A), 0.2% Rovral (Iprodione), or a controlled (water) treatment. The plants were sprayed from the onset of flowering to harvest. The berries were then stored under 100% relative humidity at room temperature. Five days following harvest, the berries were inspected for infection with grey mold (*Botrytis cinerea*). The data is shown in Table 4.

TABLE 4

| Treatment | Proportion of Berries Moldy |
|---|---|
| 1.0% $Ca(C8)_2$ | 9% |
| 0.2% Rovral | 0% |
| Untreated | 44% |

EXAMPLE 5

Four types of pathogenic fungi, identified below in Table 5, were grown on Potato Dextrose Agar, amended with the calcium salts of various fatty acids, including calcium hexanoate $(Ca(C6)_2)$, calcium octanoate $(Ca(C6)_2)$, calcium nonanoate $(Ca(C9)_2)$ and calcium decanoate $(Ca(C10)_2)$. The colonies were incubated at 22° C. for 4 to 14 days. The colony radius was measured when the fungi of the control treatment had reached the edge of a 10cm diameter petri dish, and the data is displayed in Table 5.

TABLE 5

| Calcium Salt (Concentration) | | Colony Radius (mm) | | | |
|---|---|---|---|---|---|
| | | Botrytis cinerea | Rhizoctonia solani AG4 | Fusarium oxysporum | Pythium sp. |
| $Ca(C6)_2$ | 0.5% | 0 | 21 | 0 | 0 |
| $Ca(C8)_2$ | 0.5% | 0 | 0 | 0 | 0 |
| $Ca(C9)_2$ | 0.5% | 0 | 5 | 0 | 0 |
| $Ca(C10)_2$ | 0.5% | 6 | 19 | 25 | 12 |
| $Ca(C6)_2$ | 1.0% | 1 | 11 | 1 | 0 |
| $Ca(C8)_2$ | 1.0% | 0 | 0 | 0 | 0 |
| $Ca(C9)_2$ | 1.0% | 0 | 6 | 0 | 0 |
| $Ca(C10)_2$ | 1.0% | 4 | 13 | 24 | 7 |
| Control | | 42 | 41 | 37 | 43 |
| Calcium Salt (Concentration) | | Aspergillus niger | Fusarium oxysporum | Penicillium digitatum | Penicillium sp. |
| $Ca(C8)_2$ 0.1% | | 0 | 0 | 2 | 0 |
| $Ca(C8)_2$ 0.01% | | 7 | 33 | 38 | 34 |
| $Ca(C9)_2$ 0.5% | | 0 | 0 | 0 | 0 |
| $Ca(C9)_2$ 0.05% | | 0 | 20 | 34 | 26 |
| Control | | 41 | 27 | 42 | 41 |

EXAMPLE 6

The sodium, potassium, and calcium salts of octanoic acid and nonanoic acid were applied to the leafs of 14 day old bean plants, in various concentrations, to assess the phytotoxic effect, if any, of the applied composition. The sodium, potassium, and calcium salts of octanoic acid and nonanoic were each applied in aqueous solutions at concentrations of 0.1%, 0.2%, 0.5% and 1.0%. The data shown in Table 6 illustrates the effect of phytotoxicity on the leaves of the plants caused by the applied compositions.

TABLE 6

| Chain Length (Concentration) | | Phytotoxicity (%) 3 Days After Spraying | | |
|---|---|---|---|---|
| | | Sodium | Potassium | Calcium |
| Octanoate | 1.0% | 74 | 85 | 2 |
| Octanoate | 0.5% | 31 | 48 | 1 |
| Octanoate | 0.2% | 4 | 12 | 0 |
| Octanoate | 0.1% | 0 | 3 | 0 |
| Nonanoate | 1.0% | 43 | 100 | 6 |
| Nonanoate | 0.5% | 16 | 65 | 1 |
| Nonanoate | 0.2% | 1 | 3 | 0 |
| Nonanoate | 0.1% | 1 | 0 | 0 |
| Water Control | | (0) | | |
| Untreated | | (0) | | |

EXAMPLE 7

The residual fungicidal activity of various compositions was evaluated as follows in assessing the ability to control bean anthracnose (*Colletotrichum lindemuthianum*) on 14 day old bean plants. The formulations tested included formulation A (diluted to 0.5% active ingredient), BENOMYL, a commercial fungicide available from DuPont, of Wilmington, Del., at 0.25%, and Mixture K, (diluted to 0.6% total concentration of active ingredient).

Mixture K was prepared from a concentrate having 30 weight percent ethanol, 30 weight percent water and 40 weight percent of the following potassium fatty acid salts in the following Proportions:

| | |
|---|---|
| KC6 | 1% |
| KC8 | 3% |
| KC9 | 25% |
| KC10 | 28% |
| KC12 | 35% |
| KC14 | 9% |
| KC16 | 4% |
| KC18 | 2% |
| KC18:1 | 3% |

First, the plants were sprayed with the test chemical ("Chem.") followed by inoculating the plant with spores of the fungus *Colletotrichum lindemuthianum* ("inoc."), and finally exposing the inoculated plant to 72 hours of high relative humidity to promote plant infection ("humid"). Anthracnose lesions on the leaf became visible five days after removal from the high humidity.

By changing the sequence of these steps it is possible to test the ability of a compound to surface sterilize a plant ("sterilization") to resist decomposition on the plant ("decomposition"), and to combat established infections within the plant ("established infections").

In the "sterilization treatment", a test compound is applied to the plant 1 hour after the fungal spores. This treatment tests the ability of a compound to kill spores that are already present on the plant surface. In the "decomposition" treatment fungal spores are applied to the plant 3 days after the chemical. If the compound has decomposed, many spores will survive to infect the plant and cause anthracnose lesions. In the "established infection" treatment, plants are inoculated and placed under high humidity for 3 days. During this time the spores germinate and infect the plant leaf. The test chemical is applied on the same day upon removal of the plants from the high humidity. If the compound has the ability to penetrate the leaf and to kill established infections, the number of lesions developing should be reduced.

In the "control" treatment plants are sprayed with the test chemical, but are not inoculated or exposed to high humidity. Plants of this treatment should not develop any anthracnose lesions.

The sequence of treatments to test the ability of compound to surface sterilize plants ("sterilization"), to resist decomposition on the plants ("decomposition"), and to combat established infections within the plant ("established infections") is illustrated below in Table 7. The data resulting from the treatments depicted in Table 7 are illustrated in Table 8.

TABLE 7

| Day | Sterilization | Decom-position | Established Infections | Treated Control |
|---|---|---|---|---|
| 1 | — | chem | — | chem |
| 2 | — | — | — | — |
| 3 | — | — | — | — |
| 4 | inoc/chem/humid | inoc/humid | inoc/humid | — |
| 5 | — | — | — | — |
| 6 | — | — | — | — |
| 7 | — | — | — | — |
| 8 | — | — | chem | — |
| 9 | — | — | — | — |

TABLE 7-continued

| Day | Sterilization | Decom-position | Established Infections | Treated Control |
|---|---|---|---|---|
| 10 | — | — | — | — |
| 11 | — | — | — | — |
| 12 | — | — | — | — |
| 13 | — | — | — | — |
| 14 | observations | observations | observations | observations |

TABLE 8

| | Number of Anthracnose Lesions Per Leaf | | | |
|---|---|---|---|---|
| Tmt | Sterilization | Decom-position | Established Infections | Treated Control |
| Ca(C8)$_2$ 0.5% | 0.2 | 0.0 | 40.0 | 0.0 |
| Mixture K 0.6% | 1.8 | 73.0 | 56.0 | 0.0 |
| Benomyl 0.25% | 0.0 | 0.0 | 60.0 | 0.0 |
| Water | 29.0 | 54.0 | 36.0 | 0.0 |
| Not Inoculated | 0.0 | 0.0 | 0.0 | 0.0 |

EXAMPLE 8

Little Marvel peas were sown in a soil-less potting mixture in 2.25 inch pots, and fertilized with a complete nutrient solution. Plants were grown under greenhouse conditions and sprayed weekly to runoff with the experimental solutions, starting 10 days after sowing. The experiment relied on natural infections, arising from inoculum produced on nearby infected pea plants. The final observations were made 4 days after the second spraying, and are illustrated below in Table 9.

TABLE 9

| Treatment | Proportion of the surface area of the first three leaves covered by powdery mildew colonies |
|---|---|
| Ca(C8)$_2$ 0.5% | 0.7% |
| Ca(C8)$_2$ 0.2% | 3.3 |
| Ca(C9)$_2$ 0.5% | 1.6 |
| Ca(C9)$_2$ 0.2% | 7.3 |
| Sulfur 0.42% | 0.0 |
| Water | 43.0 |
| Untreated | 80.0 |

EXAMPLE 9

Phytotoxicity and fungicidal efficacy of calcium octanoate (Ca(C8)$_2$), calcium nonanoate (Ca(C9)$_2$), and calcium decanoate (Ca(C10)$_2$) on bean anthracnose was evaluated. The fungicidal compositions were prepared according to formulation A, using the indicated fatty acid salt active ingredient, and diluting the concentrated solution to the desired concentration of active ingredient. The data is illustrated below at Table 10.

TABLE 9

| Treatment | Phytotoxicity (%) | Lesion/Length (mm/leaf) |
|---|---|---|
| Ca(C8)$_2$ 0.5% | 0.1 | 0.2 |
| Ca(C9)$_2$ 0.5% | 0.0 | 2.5 |
| Ca(C10)$_2$ 1.0% | 2.0 | 26.0 |
| Inoculated Control | 0.0 | 13.0 |

EXAMPLE 10

Little marvel peas were sown in a soil-less potting mixture in 2.25 inch pots, fertilized with a complete nutrient solution. These plants were grown under green house conditions and sprayed weekly to run-off with the experimental solutions, starting 10 days after sowing. The experiment relied on natural infections, arising from inoculium produced on nearby infected pea plants. The final observations were made 4 days after the second spraying. The experiment assessed the control of pea powdery mildew (*Erysiphe communis*) using as active ingredients calcium octanoate, calcium nonanoate, Mixture K, BENOMYL, and sulfur. The calcium octanoate and nonanoate were prepared according to formulation A while mixture K was prepared as described in Example 7. The BENOMYL and sulfur are commercially available compositions. The data is shown below in Table 11.

TABLE 11

| Treatment | Phytotoxicity (%) | Proportion of the surface area of the first three leaves covered by powdery mildew colonies |
|---|---|---|
| Ca(C8)$_2$ 1.0% | 0.3% | 0.0% |
| Ca(C9)$_2$ 1.0% | 0.1 | 0.0 |
| Mixture K 0.6% | 4.0 | 0.0 |
| Sulfur 0.42% | 0.0 | 0.0 |
| Benomyl 0.25% | 0.0 | 0.0 |
| Water | 43.0 | 5.0 |
| Untreated | 80.0 | 9.6 |

It is understood that various modifications described herein may be made without exceeding the scope of the invention.

What is claimed is:

1. An environmentally compatible, non-phytotoxic fungicidal composition, consisting essentially of:
   a fungicidally effective, non-phytotoxic active ingredient at a concentration of about 0.05 to 1 percent by weight of the composition, the active ingredient is selected from the group consisting of one or a mixture of metal salts of alpha monocarboxylic fatty acids having from 8 to 12 carbon atoms, wherein the salts are formed from metals selected from the group consisting of calcium, copper, iron, and zinc, the salts being present as suspended solids and being substantially insoluble;
   a gum component selected from the group consisting of xanthan gum, locust bean gum, acacia gum, magnesium aluminum silicate, sodium alginate, gelatin, and mixtures thereof;
   one or more wetting agents; and
   water.

2. The composition of claim 1, further comprising one or more dispersants, present at a range of 2 to 15 percent by weight of the total composition.

3. The composition of claim 1, further comprising a component which inhibits freezing of the composition, present at approximately 1.0 to 10 percent by weight of the total composition, the component being selected from the group consisting of propylene glycol, ethylene glycol, glycerine and isopropyl alcohol.

4. The composition of claim 1, further comprising an alcohol.

5. The composition of claim 1 wherein the fatty acid metal salt active ingredient is the Ca$^{+2}$, Cu$^{+1}$, Cu$^{+2}$, Fe$^{+2}$, Fe$^{+3}$, or Zn$^{+2}$ salt of one or a mixture of alpha monocarboxylic acids selected from the group consisting of octanoic acid, nonanoic acid, decanoic acid, undecanoic acid, undecenoic acid and dodecanoic acid.

6. The composition of claim 1 wherein the fatty acid metal salt active ingredient is selected from the group consisting of calcium octanoate, calcium nonanoate and mixtures thereof.

7. An environmentally compatible, non-phytotoxic fungicidal composition, consisting essentially of:
   approximately 0.05 to 1 percent by weight of a fungicidally effective, non-phytotoxic fatty acid metal salt active ingredient selected from the group consisting of one or a mixture of the metal salts of octanoic acid, nonanoic acid, decanoic acid, undecanoic acid, undecenoic acid, and dodecanoic acid where the salts are formed from metals selected from the group consisting of calcium, copper, iron, and zinc, and wherein the salts are present as suspended solids and are substantially insoluble in water;
   approximately 0.5 to 5 percent by weight of a gum component selected from the group consisting of xanthan gum, locust bean gum, acacia gum, magnesium aluminum silicate, sodium alginate, and mixtures thereof;
   approximately 2.0 to 10.0 percent by weight of an anti-freezing composition selected from the group consisting of propylene glycol, ethylene glycol, glycerine, and isopropyl alcohol;
   approximately 0.5 to 10 percent by weight of a dispersant;
   approximately 0.5 to 5 percent by weight of wetting agent; and
   the balance made up by water.

8. An environmentally compatible, non-phytotoxic fungicidal composition, consisting essentially of:
   a fungicidally effective, non-phytotoxic first active ingredient at a concentration of about 0.05 to 1 percent by weight of the composition, the active ingredient comprising one or a mixture of metal salts of alpha monocarboxylic fatty acids having from 8 to 12 carbon atoms, wherein the salts are formed from metals selected from the group consisting of calcium, copper, iron, and zinc, the salts being present as suspended solids and being substantially insoluble in water;
   a second active ingredient selected from the group consisting of sulfur, lecithin and a lecithin-containing composition;
   a gum component selected from the group consisting of xanthan gum, locust bean gum, acacia gum, magnesium aluminum silicate, sodium alginate, gelatin, and mixtures thereof, the gum component being present in a concentrated formulation at approximately 0.5 to 10 percent by weight of the total composition;
   one or more wetting agents, present in a concentrated formulation at a range of about 2 to 15 percent by weight of the total composition; and
   water.

9. A method of protecting living plants from infection by pathogenic fungi, comprising the steps of applying the composition of claim 1 to living plants.

10. A method of protecting living plants from infestation by pathogenic fungi, comprising the step of applying the composition of claim 1 to living plants.

11. A method of protecting living plants from infestation by pathogenic fungi, comprising the steps of:
   providing an anti-fungal, non-phytotoxic composition consisting essentially of a gum component, one or more wetting agents, and a fatty acid metal salt active ingredient selected from the group consisting of calcium octanoate, calcium nonanoate and mixtures thereof, the fatty acid metal salt active ingredient being present as suspended solids and being substantially insoluble in water;
   diluting the composition with water such that the concentration of the active ingredient is in the range of about 0.05 to 1 percent by weight; and
   applying the composition to living plants.

* * * * *